US008065094B2

(12) United States Patent
Statham

(10) Patent No.: US 8,065,094 B2
(45) Date of Patent: Nov. 22, 2011

(54) METHOD OF CALCULATING THE STRUCTURE OF AN INHOMOGENEOUS SAMPLE

(75) Inventor: Peter John Statham, Bucks (GB)

(73) Assignee: Oxford Instruments Nonotechnology Tools Unlimited, London (GB)

( * ) Notice: Subject to any disclaimer, the term of this patent is extended or adjusted under 35 U.S.C. 154(b) by 589 days.

(21) Appl. No.: 12/182,597

(22) Filed: Jul. 30, 2008

(65) Prior Publication Data

US 2010/0030488 A1    Feb. 4, 2010

(51) Int. Cl.
*G01N 33/00*    (2006.01)
(52) U.S. Cl. ............ 702/28; 702/22; 250/310; 250/307; 250/390.07; 378/44; 378/45; 378/46; 378/48; 378/50; 378/83; 378/113; 378/124
(58) Field of Classification Search ............... 702/28, 702/40, 134, 137, 173, 180, 181, 183, 189, 702/190, 194, 196, 197; 250/306–311, 336.1–395; 378/44, 45, 46, 47, 50, 53
See application file for complete search history.

(56) References Cited

U.S. PATENT DOCUMENTS

| | | | | |
|---|---|---|---|---|
| 4,260,885 A * | 4/1981 | Albert | ............................ | 378/45 |
| 5,299,138 A * | 3/1994 | Fiori et al. | ...................... | 702/22 |
| 6,118,850 A * | 9/2000 | Mayo et al. | ..................... | 378/83 |
| 6,349,128 B1 * | 2/2002 | Nelson | ............................ | 378/44 |
| 6,675,106 B1 * | 1/2004 | Keenan et al. | .................. | 702/28 |
| 7,016,462 B1 * | 3/2006 | Keville et al. | ................... | 378/47 |
| 7,132,652 B1 * | 11/2006 | Testoni | .......................... | 250/310 |
| 7,166,838 B1 * | 1/2007 | Janik | ............................. | 250/310 |
| 2002/0097834 A1 * | 7/2002 | Satoh | ............................. | 378/46 |

(Continued)

FOREIGN PATENT DOCUMENTS

WO    WO2007/132243    11/2007

OTHER PUBLICATIONS

Raynald Gauvin, "Quantitative X-Ray Microanalysis of Heterogeneous Materials Using Monte Carlo Simulations", Microchim Acta 155, May 4, 2006, pp. 75-81, Springer-Verlag 2006.

(Continued)

*Primary Examiner* — Carol Tsai
(74) *Attorney, Agent, or Firm* — Blank Rome LLP

(57) ABSTRACT

A method is provided of calculating the structure of an inhomogeneous sample in which an electron beam is used to cause excitation of x-rays from the sample under known conditions of beam energy and geometry with respect to the sample. Notably the beam current is unknown. Measured x-ray intensity data for the sample corresponding to one or more sets of beam conditions and beam currents are firstly obtained, together with comparative x-ray intensity data for samples having known structures. A beam current factor for each beam condition is estimated and effective x-ray intensity data for each of the sets of conditions are then calculated using the measured and comparative x-ray intensity data and the beam current factor. The structure of the sample is then calculated for each of the sets of conditions using the effective x-ray intensity data. Predicting x-ray intensity data are produced corresponding to the calculated structure and compared with the effective x-ray intensity data. These steps are repeated using revised beam current factors until the predicted and effective x-ray intensity data achieve a predetermined similarity condition.

31 Claims, 4 Drawing Sheets

U.S. PATENT DOCUMENTS

2004/0099805 A1* 5/2004 Ochiai et al. .................. 250/311
2006/0049349 A1* 3/2006 Shemesh ...................... 250/310
2007/0092060 A1* 4/2007 Grodzins ........................ 378/50

OTHER PUBLICATIONS

Peter Duncumb, Ian R. Barkshire, Peter J. Statham, "Improved X-ray Spectrum Simulation for Electron Microprobe Analysis", Microscopy and Microanalysis, 7, pp. 341-355, 2001.

Jean-Louis Pouchou, "X-Ray Microanalysis of Stratified Specimens", Analytica Chimica Acta, 283, pp. 81-97, 1993.

Peter J. Statham, "Deconvolution and Background Subtraction by Least-Squares Fitting with Prefiltering of Spectra", Analytical Chemistry, vol. 49, No. 14, pp. 2149-2154, Dec. 1977.

Jean-Louis Pouchou, "X-Ray Microanalysis of Thin Surface Films and Coatings", Mik rochimica Acta 138, pp. 133-152, Springer-Verlag 2002.

Numerical Recipes In C: The Art of Scientific Computing, Chapter 15, "Modeling of Data" 1992, pp. 656-706, Numerical Recipes Software; Second Edition, W.H. Press et al., Cambridge University Press 1999.

* cited by examiner

METHOD OF CALCULATING THE STRUCTURE OF AN INHOMOGENEOUS SAMPLE

FIELD OF THE INVENTION

The present invention relates to a method of calculating the structure of an inhomogeneous sample in which an electron beam is used to cause excitation of x-rays from the sample under known conditions of beam energy and geometry with respect to the sample. Importantly, in the method, the beam current is unknown. Furthermore, the method does not require the measurement of a standard.

BACKGROUND OF THE INVENTION

One important method of analysing inhomogeneous samples, such as multiple thin layers on a substrate, involves exposing a specimen to a beam of electrons and measuring the emitted x-ray spectrum. Provided the electron beam is sufficiently energetic to penetrate through the layers and reach the substrate, then characteristic x-rays are generated from elements in both the substrate and the various layers and these contribute to the total x-ray spectrum seen by an x-ray detector.

FIG. 1 shows a typical situation where a 10 keV electron beam is incident on a layered sample with three layers of different thickness on a substrate. Many electron trajectories are shown and x-rays may be generated at any point along the electron trajectory as a result of ionisation of atoms. X-rays are emitted in all directions and if an x-ray detector is positioned above the sample, then x-rays emitted towards the detector will provide signals representative of the elements present in the regions excited by the electron beam. In the arrangement of FIG. 1, x-rays will emerge from all three layers and from the substrate. In FIG. 2, the same sample is exposed to a lower energy electron beam. In this case, the electrons only penetrate into the top two layers so there will be no signal from the lowest layer and the substrate. In general, if a series of x-ray spectra are acquired at different incident electron beam energies, typically between 2 keV and 20 keV, then the corresponding spectra will exhibit characteristic x-ray peaks that vary according to the thicknesses and the compositions of the various layers, and indeed the substrate.

Given a particular electron beam energy, the characteristic intensity for a particular element within a multi-layered sample can be expressed as a "k-ratio". A "k-ratio" is the ratio of the x-ray intensity received for a particular element from the structure (counts per second recorded from a characteristic x-ray emission series such as K, L or M) to that obtained from a flat bulk specimen of pure element under the same experimental conditions. As the name suggests, a k-ratio is dimensionless. Taking this ratio avoids having to know the x-ray detector collection efficiency as a function of energy. By measuring a series of k-ratios, it is sometimes possible to deduce the thicknesses and compositions of the various layers in a multi-layer specimen. Whether this is possible or not depends upon the x ray data, the extent to which information is known about the sample and experimental conditions, and the number of unknowns.

If NE elements in total occur in one or more of the layers or in the substrate and there are NL layers with thickness $T1, T2 \ldots TNL$, and layer L contains concentration $CL_j$ of element j, and the substrate contains concentration $CS_j$ of element j then the predicted k-ratio for element i at incident electron beam energy $E0$ can be written as Equation 1 below:—

$$ki = fi(E0, T1, T2, \ldots TNL, C11, C12, \ldots C1NE, C21, C22 \ldots C2NE, \ldots CNL1, CNL2, \ldots CNLNE, CS1, CS2, \ldots CSNE) \quad \text{Equation 1:}$$

where fi is a non-linear function of the layer thicknesses and the compositions of the layers and substrate. Several equations of this form cover the measured element intensities at this one beam energy $E0$.

There may be more than one equation for a particular element if measurements are made on more than one x-ray emission series for this element (e.g. K or L or M emissions). Measurements may also be taken at further values of the beam energy and in general there will be M of these non-linear equations for k-ratios. The function in Equation 1 typically involves integrations and non-linear functions and in general it is not possible to "invert" the set of equations and write down a formula that expresses the thickness or compositions for any one layer in terms of a set of measured k-ratios. Therefore, to determine a set of thicknesses and compositions ("layer variables") from a set of x-ray measurements, it is known to use a modelling approach where the parameters of the model are adjusted to find a set of ki that are a "best-fit" to the measured k-ratios (see for example, Chapter 15 in "Numerical Recipes in C", Second Edition, W.H. Press et al, Cambridge University Press 1999). Thus, a computer program is used to make iterative guesses at the thickness and composition of the layers to find a set that is a close fit with the k-ratios measured from x-ray spectra (see for example, J. L. Pouchou. "X-ray microanalysis of stratified specimens", Analytica Chimica Acta, 283 (1993), 81-97. This procedure has been made available commercially in the software product "Stratagem" by SAMx, France). The computer program will make a test at each iteration to see if the guesses are not changing significantly between iterations, in which case "convergence" is achieved. Unfortunately in some cases, it is impossible to find a best-fit set of thicknesses and compositions because the measured k-ratios do not reveal enough differences in intensity to resolve the source of the individual contributions to x-ray intensity. In this case, the computer program iterations will fail to converge on a unique solution. Such problems can sometimes be resolved by choosing different x-ray emission series, different beam energies or constraining the range of possible solutions by providing information on some of the thicknesses or compositions where this is known beforehand.

Although there are some guidelines for the choice of beam energies and x-ray series (see for example, J. L. Pouchou, "X-ray Microanalysis of Thin Films and Coatings", Microchim. Acta 138, 133-152 (2002)), in general it is difficult to prove that a given type of sample can always be analysed successfully by this technique except by extensive experimentation in the hands of an expert.

A further practical difficulty arises in obtaining measured k-ratios. With a given beam current incident on the multilayered specimen, the x-ray intensity for an elemental line is measured by recording x-ray counts in a known time interval. A pure element standard is then placed under the beam and the x-ray intensity is measured. The ratio of the two intensities is the measured k-ratio. If a pure element standard is not available for the element in question, then a compound standard could be used or a pure standard from a different element. In that case, a correction is required to convert the measured intensity to that which would have been obtained from a pure standard of the element in question. Besides the inconvenience of having to have both specimen and standard accessible on the same specimen stage, a critical requirement is that the beam current and incident electron energy must be identical for the measurements on the specimen and standard.

In some specialised instruments, it is possible to obtain a direct measure of incident electron beam current and this can be used in principle to make a correction if a different current is used for specimen and standard measurement provided the beam current measuring equipment is correctly calibrated. However, in general, analysis instruments are not provided with apparatus which is able to accurately measure the beam current since such apparatus is costly and also takes time to stabilize.

For the conventional case of analysis of a homogeneous bulk material, it is well known that analysis is possible without the use of standards or beam current measurements, provided all unknown elements emit lines that can be measured and the total concentration is assumed to be 100%. However, as pointed out previously (J. L. Pouchou. "X-ray microanalysis of stratified specimens", Analytica Chimica Acta, 283 (1993), 81-97): "Contrary to the case of conventional analysis of homogeneous microvolumes, it is not easy in the case of stratified specimens to work with no standard at all, because this would require to know very accurately the beam current and the solid angle of detection." Furthermore, in some electron beam instruments such as cold field emission scanning electron microscopes, beam current fluctuations make comparative measurements difficult (e.g. R. Gauvin, "Quantitative X-Ray Microanalysis of Heterogeneous Materials Using Monte Carlo Simulations", Microchim Acta 155, 75-81 (2006)).

Thus, there are two undesirable problems with the electron-excited x-ray analysis of inhomogeneous materials such as multilayered materials: the difficulty of determining the feasibility of performing me required analysis and the difficulty of measuring k-ratios using the same equivalent beam current. The problem of determining feasibility has been addressed in our previous patent application, the contents of which are incorporated herein by reference in their entirety (WO2007/132243).

One technique for overcoming the beam current difficulty for some specific situations has been described where measurements of film and substrate element line intensities are used to form a ratio which is independent of beam current (Raynald Gauvin, Quantitative X-Ray Microanalysis of Heterogeneous Materials Using Monte Carlo Simulations, Microchim Acta 155, 75-81 (2006)). This ratio can be used in a calibration curve method to determine either the thickness of a single pure element film on dissimilar pure element substrate or the diameter of a pure element sphere on a dissimilar pure element substrate. However, since the ratio involves different element x-ray lines, the detector efficiency does not cancel as it does for a k-ratio and a calibration factor has to be determined for each application.

SUMMARY OF THE INVENTION

In accordance with a first aspect of the invention we provide a method of calculating the structure of an inhomogeneous sample in which an electron beam is used to cause excitation of x-rays from the sample under known conditions of beam energy and geometry with respect to the sample, and wherein the beam current is unknown, the method comprising:—
i) obtaining measured x-ray intensity data for the sample, the data corresponding to one or more sets of beam conditions and beam currents;
ii) obtaining comparative x-ray intensity data for samples having known structures;
iii) estimating a beam current factor for each beam condition;
iv) calculating effective x-ray intensity data for each of the sets of conditions using the measured and comparative x-ray intensity data and the beam current factor;
v) calculating the structure of the sample for each of the sets of conditions using the effective x-ray intensity data;
vi) predicting x-ray intensity data corresponding to the calculated structure;
vii) comparing the predicted and effective x-ray intensity data;
viii) repeating steps (iii) to (vii) using beam current factors revised in accordance with step (vii) until the predicted and effective x-ray intensity data achieve a predetermined similarity criterion.

We have realised that it is possible to determine the structure of an inhomogeneous sample without the need to measure beam currents and also without the need to use a physical reference standards as part of the method. The method involves measuring x-ray intensities for one or more elements present in the sample when it is excited by an electron beam. A series of relative x-ray intensities emitted by pure elements when excited by a constant-current electron beam is obtained by known methods, notably the excitation conditions having the same energy and geometry as that used for the specimen measurements. The beam current is not known in either of the above steps although in order to calculate the structure a value must be attributed to the beam current. This is deduced by calculation. However, the calculation of the structure of the sample and the beam current are interrelated and the final calculated structure of the sample and the beam current are thus arrived at by a repeated process which involves the prediction of the x-ray data which would be measured in practice for a given calculated structure. The method can be performed for one set of x-ray measurements under a single set of conditions. However, further advantage is derived if multiple conditions (different beam energies and/or geometries) are used since these provide additional information concerning the structure and allow more unknowns within the structure itself to be determined as part of the structure calculation.

We note here that the structure of the sample preferably includes a full description of the component parts of the structure which make it inhomogeneous (including their size and distribution) such as layers, porosity, grains, fibres and so on; together with the elemental composition of all such component parts. The calculation of the structure according to step (v) uses structure data defining physical parameters and composition parameters of the structure. Part of the structure data therefore comprises unknown physical parameters or unknown composition parameters or unknown physical and composition parameters.

A typical inhomogeneous structure is a multi-layer specimen and in this case, the parameters describing the structure would be the physical dimensions such as the thicknesses, and the elemental compositions of the layers (including any substrate). The method provides for the determination of such parameters, provided there is enough information content in the measurements to resolve unique values for those parameters. The information content in the measured x-ray spectrum can be altered by changing the incident electron beam energy and/or geometry, in this context, the "geometry" refers to the relative orientation of incident beam direction to the sample normal and to the relative orientation of direction for emitted x-rays to reach the x-ray detector. A higher energy beam penetrates further into the sample and reveals more information about material at greater depths. A shallow entry angle for the beam confines excitation more to the surface layers and a shallow take-off-angle for x-rays increases absorption for x-rays generated at greater depths. Note that the method can be modified for other inhomogeneous samples such as a determination of the composition and size of a spherical particle upon a substrate. A multilayer specimen consisting of two layers on a substrate would be soluble for thickness of the individual layers, provided that composition of each layer was known and there was at least one element unique to each layer. A Monte Carlo simulation method could be used to predict intensities for arbitrary shapes and compositions. The case of a spherical particle on a substrate would be soluble for thickness, provided the assumption that the particle is spherical is valid. For more exotic shapes, a "solubility check" would be advisable to see if the problem was soluble; for Monte Carlo approach, numerical differentiation can be used in this case to build the Jacobian that is used to test for solubility (see our earlier patent application WO2007/132243).

Typically the comparative x-ray intensity data are obtained by a method selected from the group of: calculation according to a model, physical measurement of standard samples of pure elemental composition, physical measurement of standard samples of compounds of known composition wherein corresponding pure elemental contributions are calculated. For example, at each beam energy and geometry condition, a series of x-ray line intensities may be measured for all available line emissions. This would usually be obtained by analysis of a single recorded x-ray spectrum. When a beam of the same energy and geometry and beam current is incident on various pure element specimens ("standards"), the intensity can be measured for emission lines for those pure elements. If the beam current can be measured then intensities measured with different beam currents can be scaled to correspond to the same beam current value. This could form a calibration procedure for the instrument for a certain beam energy and the relative pure element x-ray line intensities can be stored in a database. Alternatively, standards of known composition could be measured and the x-ray line intensities converted by suitable correction procedures into the corresponding x-ray line intensities that would be generated for pure element standards. A further alternative would be to rely on theoretical prediction of x-ray intensities from pure elements for a particular x-ray detector, in general the comparative x-ray intensity data is in the form of data normalised with respect to a particular element such as cobalt.

By any one of these methods, it is possible to determine all the intensities that would have been obtained from pure elements, scaled by a single unknown factor that is proportional to the beam current. If each measured x-ray line intensity from the inhomogeneous specimen measurement is divided by the intensity that would be generated from a pure element for the same beam current and incident beam energy, the "k-ratio" is determined. We note here that "k-ratio" is the term commonly used in the field of electron beam x-ray analysis and for a single element it is possible to calculate or measure a k-ratio from any emission line that is excited such as K, L or M. Even at the same incident beam energy, for a given element, the k-ratios for K, L or M line emissions will in general be quite different and each k-ratio provides additional information on the sample structure. Thus, using a stored database of measured or calculated relative intensities for pure elements at the same beam energy, the measured x-ray line intensities from the specimen can be converted to a set of k-ratios apart from a common unknown multiplicative constant. If more than one beam energy is used to collect x-ray intensity values, then there will be an unknown and different multiplicative constant for each beam energy.

The beam current factor is one of the "unknowns" to be determined by the method. Since the method normally involves repetition of the steps (iii) to (vii) so as to converge the calculation of the structure and the beam current factor, an initial estimate of the beam current factor is needed. Such an initial estimate of the beam current factor in step (iii) may be calculated by:

a) using structure data defining an assumed structure of the sample to calculate assumed k-ratio data for the sample, the structure data including assumed values for any unknown parameters of physical structure or composition; and, b) dividing the sum of the values for the assumed k-ratio data by the sum of the values of the measured k-ratio data for the particular set of conditions and beam current in question.

Note that it would be possible to work from measured x-ray intensities (rather than k-ratios). These intensities depend on the efficiency of the detector at each x-ray energy, whereas advantageously the k-ratio is independent of detector efficiency.

Alternatively, the initial estimate of the beam current factor in step (iii) may be calculated as the inverse of the sum of the measured k-ratio data. Note that a beam current factor is used since it is not essential to calculate the beam current itself in absolute terms.

To determine the unknown parameters defining the inhomogeneous structure, an initial estimate may be made using a combination of parameters that are already known; parameters that can be derived from other parameters; and the unknown parameters. A theoretical model for the inhomogeneous structure is then used to predict x-ray intensity data (typically as k-ratios) for all the available elemental x-ray lines that would be excited by each incident beam energy and geometry condition. Additional estimates are made of the beam current scaling factors for each condition and used together with the database to generate measured k-ratios for all emitted x-ray lines under each condition. The measured and predicted k-ratios are then used to refine the estimates of the unknown parameters. This preferably involves the use of a structure solver model in which measured x-ray data and other experimental parameters (such as beam-sample geometry and beam energy) are used to produce a prediction of the structure of the sample, specifically giving values to the unknown parameters of the structure.

A process of iteration may be used to refine the estimates of the unknown structure parameters until the effective measured and predicted k-ratios achieve the closest match possible (such a closest match being an example of a predetermined similarity criterion). Ideally, each predicted k-ratio should only differ from the measured k-ratio by an amount which is of the same order as the statistical error in the measurement of k-ratio. In practice, the theoretical prediction of k-ratios is not perfect and the measurement of k-ratios may be subject to systematic errors in addition to random statistical errors. Therefore, provided the predicted and measured k-ratios are within a predetermined relative difference for example, the iterative process is deemed to have succeeded and is continued until no significant improvement can be achieved in the "similarity measure" used to compare the predicted and measured k-ratios. A typical similarity measure would be the sum of squared differences between predicted and measured k-ratios, weighted inversely according to the expected statistical variances of the measured k-ratios. The comparison step (vii) may include calculating the simple sum of the squared differences between the values of the predicted and effective measured x-ray intensity data, or indeed one of a number of alternative methods of determining convergence.

In general the similarity criterion is met when a numerical measure of the difference between the values of the predicted and effective x-ray intensity data achieves the smallest value possible by iteration.

Thus, at each iteration, the similarity measure (e.g. sum of squares of differences) is calculated and a new estimate of the beam current factor is also calculated for each beam condition. The best similarity measure result is recorded (closest match so far). If the match cannot be bettered by adjusting the values of the beam current factors, or the new estimates of beam current factors are all within a prescribed limit of factors that have already been tried, then the iteration is deemed to have converged and the similarity criterion is met.

Each beam current scaling factor effectively adds an additional unknown to be determined and there must be sufficient measured x-ray lines and sufficient information content in order to make the problem soluble. While it is necessary to have at least as many line intensity measurements as there are unknowns to be determined, this is not a sufficient condition for the problem to be soluble.

This "feasibility" problem (for unknowns in physical dimension and composition) has been addressed in prior patent application (WO2007/132243) using the following approach. The theoretical model for x-ray emission from an inhomogeneous material is considered as a set of non-linear functions, $f_i$, of the unknown parameters (for example, thicknesses and/or compositions of a multilayered specimen), Tj, which gives the k-ratio ki for each emitted elemental line: $k_i = f_i(T_1, T_2, \ldots T_j \ldots T_N)$. This "forward" model will always give a value for $k_i$ for any combination of $T_j$ and numerical differentiation can be used to estimate the partial derivative $(\partial K_i/\partial T_j)$. For the M k-ratios and N unknown parameters, the M×N matrix of partial derivatives is the Jacobian, J, for $f_i$ with respect to the N unknown parameters at a point in the space spanned by permitted values for the unknown parameters. Singular-value decomposition, SVD, is used to factorise J to find the "inverse condition number". ICN, the ratio of the smallest to the largest singular value and to construct the pseudo-inverse of J. If ICN=0, the problem is insoluble but if ICN exceeds some threshold, say 0.1, then the iterative method to find a best-fit set of unknown parameters has a chance of converging successfully to a unique solution. By evaluating ICN for different values of incident beam energy and/or geometry, it is possible to investigate whether there is any condition for which the problem can be solved using a single excitation condition. If one condition is not enough, then measurements at a second condition can be added. This usually increases the number of measurements available without increasing the number of unknown parameters. The Jacobian is simply extended to include the partial derivatives for the second condition. Similarly, the automatic investigation of feasibility of the structure analysis process can be extended to any number of sets of conditions.

This procedure to establish feasibility can be exploited with the current invention to include unknown beam currents because when beam current measurements are excluded, this effectively introduces one additional unknown parameter for every excitation condition used and the partial differentials for k-ratios with respect to beam current variation are straightforward to evaluate because all k-ratios at a particular excitation condition are directly proportional to incident beam current. Thus, the Jacobian of partial derivatives can be constructed and ICN evaluated for the situation where beam current measurement is to be avoided.

If the database of relative intensities for pure element lines is accurate and is appropriate to the particular system being used to detect x-rays, then "standardless" analysis becomes possible where the incident beam is placed on the specimen of interest and analysis results for unknown structure parameters are determined without having to reposition a standard under the beam to make a reference measurement. The potential for standardless analysis and the ability to obtain results with an unstable beam current, as may be the case in high resolution cold field emission gun scanning electron microscopes, are key benefits of the invention.

BRIEF DESCRIPTION OF THE DRAWINGS

An example of a method according to the invention is now described with reference to the accompanying drawings, in which:—

DESCRIPTION OF EMBODIMENTS

Figure 1:
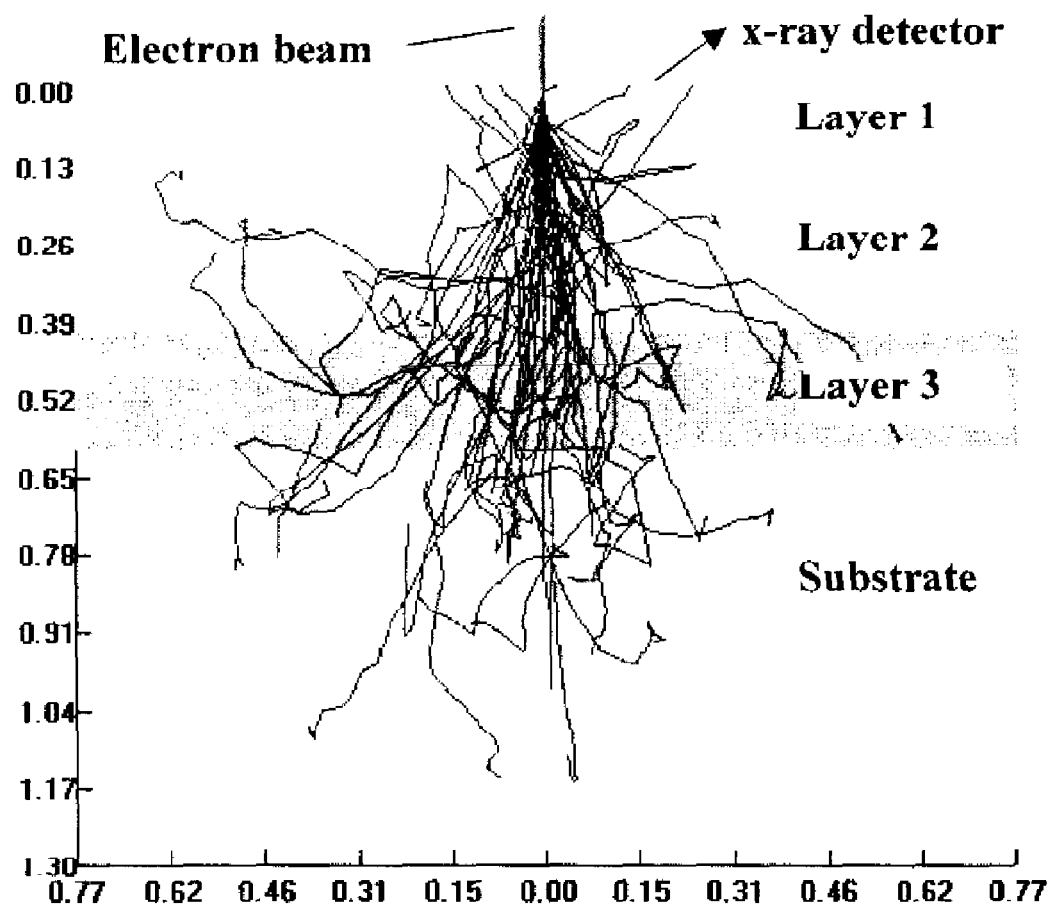
FIG. 1 shows the penetration of an electron beam into a multilayered sample.
Figure 2:
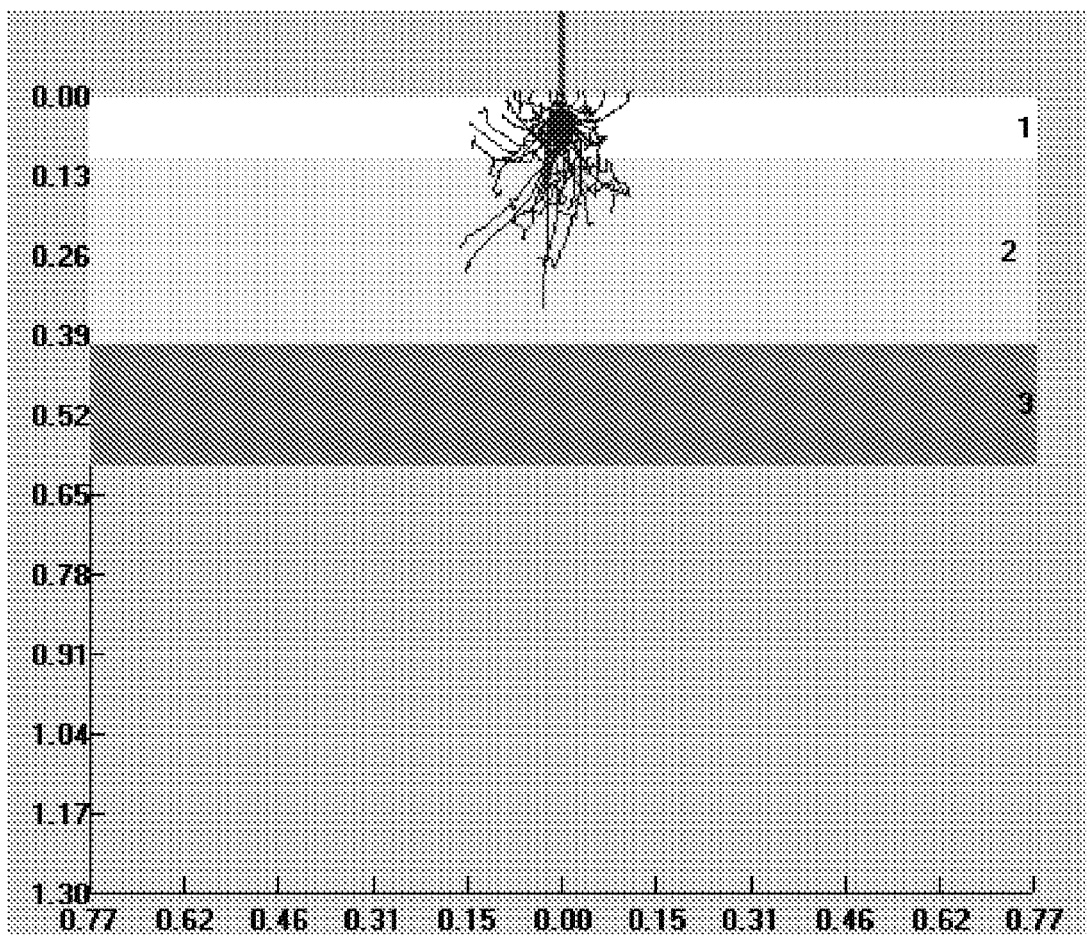
FIG. 2 shows the penetration of an electron beam having a lower beam energy than in FIG. 1.
Figure 3:
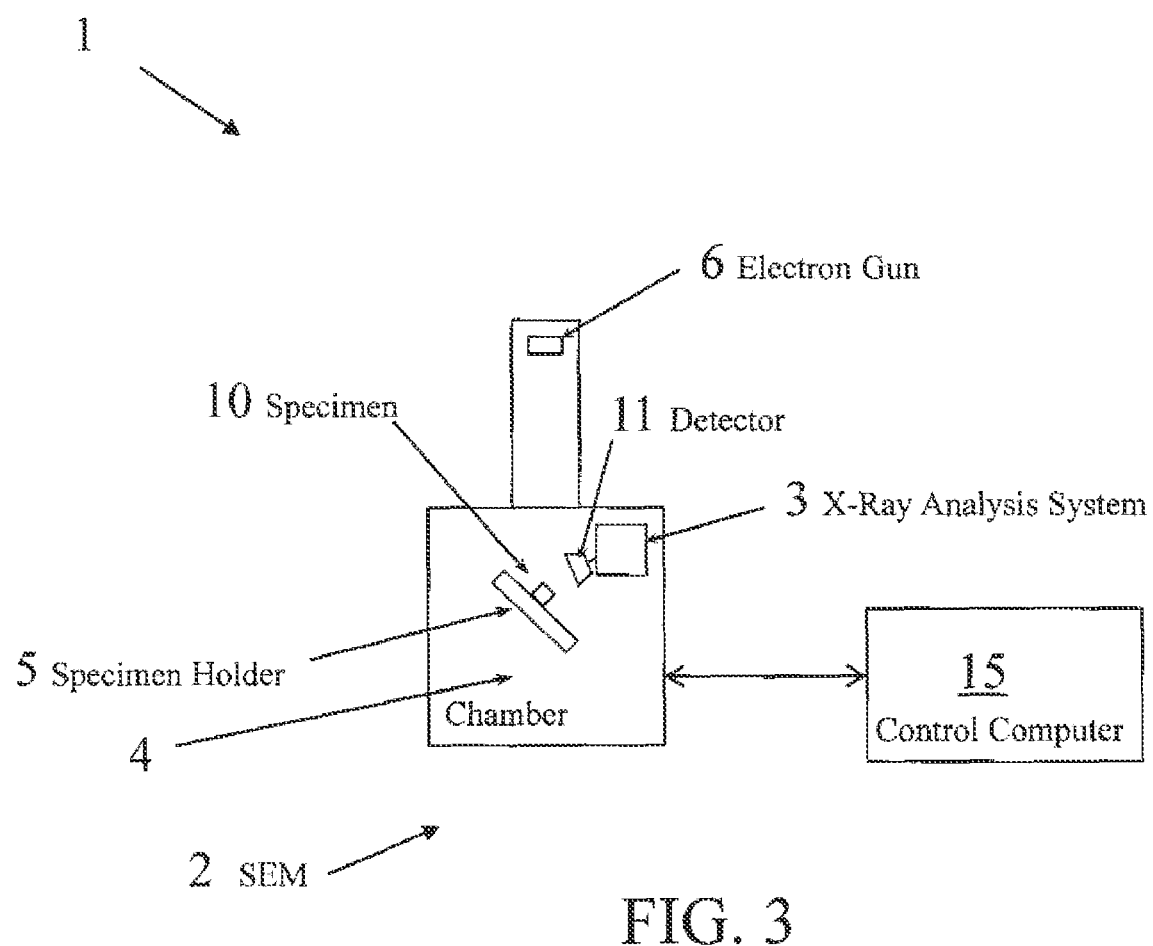
FIG. 3 is a schematic illustration of apparatus for performing a proposed structure analysis process; and, FIG. 4 is a flow diagram illustrating a first example method according to the invention.

An overview of a physical system 1 for performing a structure analysis process of inhomogeneous samples (such as thin films) is shown in FIG. 3. The system comprises a scanning electron microscope (SEM) 2 having an x-ray analysis system 3, this being an INCA Energy x-ray analysis system (manufactured by Oxford Instruments Analytical Limited). The SEM has a chamber 4 containing a specimen holder 5 which can be tilted. An incident beam of electrons is emitted by an electron gun 6, this being focused upon a specimen 10 held within the specimen holder. Characteristic x-rays that are emitted as a result of the electron beam are detected by a detector 11 forming part of the x-ray analysis system 3. The SEM 2 includes a control computer 15 upon which software is executed to control the operation of the system 1. This computer can control the kV used to accelerate electrons from the electron gun 6 and thus alter the energy for the focused electron beam striking the specimen. To analyse the specimen 10, an electron beam energy and beam current is selected and an x-ray spectrum is acquired for a chosen acquisition time. Element peak intensities are obtained from the spectrum using a suitable method (for example "Deconvolution and background subtraction by least squares fitting with prefiltering of spectra", P J Statham, Anal. Chem. 49, 2149-2154, 1977 incorporated herein by reference). According to the known prior art technique, while the experimental conditions are stable, a known standard is moved under the beam into the same position occupied by the specimen 10 and a reference x-ray spectrum is obtained from the standard. The spectrum from the standard measurement is used to obtain the peak intensities that would be obtained from a flat sample of bulk pure element for each of the elements in the specimen to be analysed. Either a series of pure element or compound standards are used according to the prior art method, or a single standard can be used and the corresponding intensities worked out by applying calculated scaling factors to the appropriate standard measurement (see for example the operating manual for the thin film program "Stratagem" sold by SAMx, France). In the present invention the use of standards within the same apparatus is not required which is extremely advantageous. However, this does mean that the information which is obtained from the standards in the prior art method must be obtained by other means according to the present invention.

Figure 4:
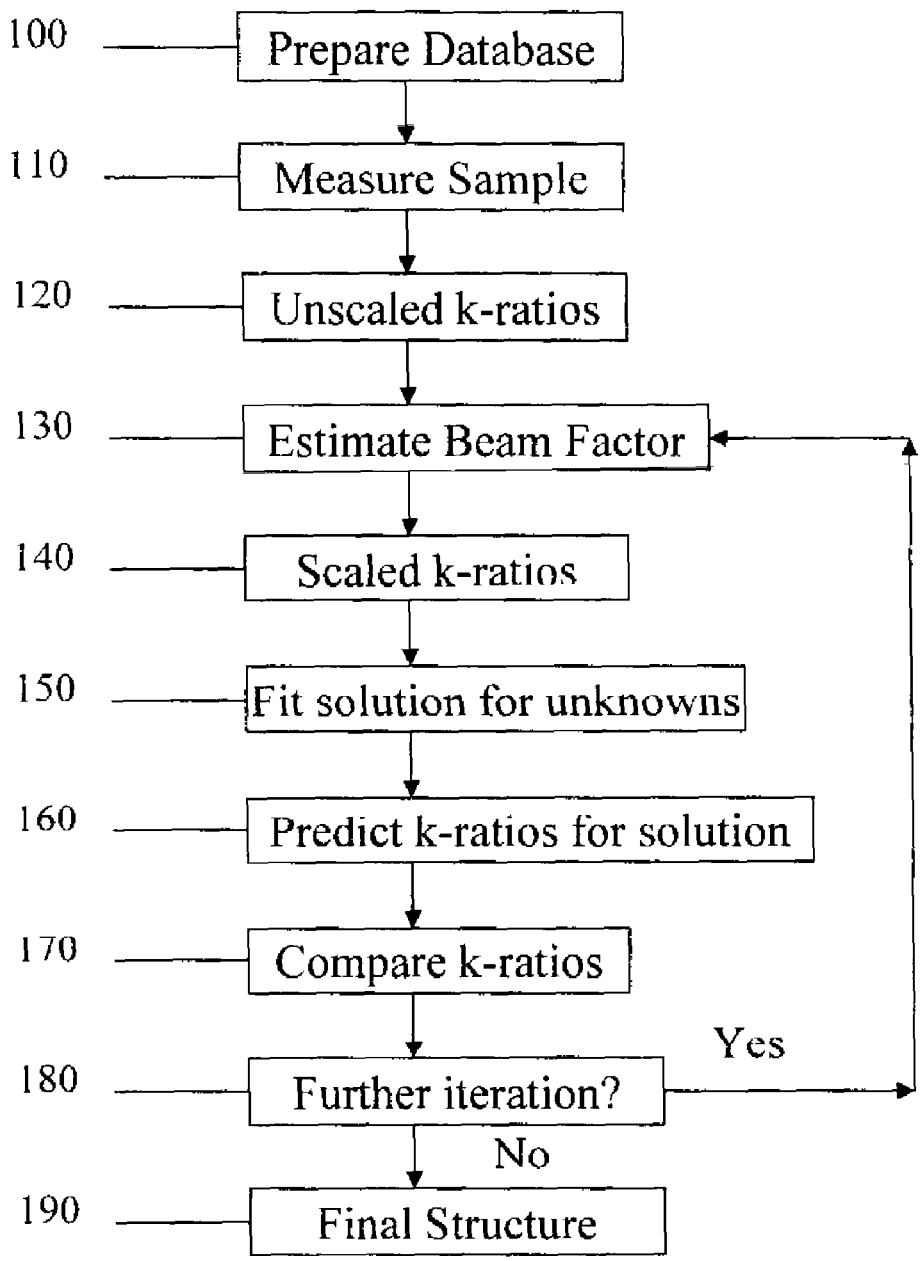

Referring now to FIG. 4, at step 100, a database is prepared that includes the x-ray intensities of pure elements obtained for a given beam energy, sample geometry and detector configuration. For example, a set of polished pure element standards can be prepared together on a single specimen mount. Suitable "standard blocks" are commercially available and are commonly used for electron probe micro analysis using x-rays. Such a standard block is mounted on the scanning electron microscope (SEM) specimen stage and the accelerating voltage is set to provide the desired incident beam energy. The beam is positioned on one of the pure element standards and an x-ray spectrum is recorded with the current x-ray spectrometer for a given time interval. Without adjusting the beam current, the standard block is moved so that the beam is positioned on a different standard and an x-ray spectrum recorded for the same time interval. By analyzing each spectrum, the intensity of each pure element line can be determined. A series of intensities for different elements are thus obtained at the same beam current. For convenience, these intensities are ratioed to the intensity of one particular standard (for illustrative purpose, this could be the Cobalt K intensity). If there are different standard blocks with different elemental standards, then provided there are some standards in common between the blocks, it is possible to build up a set of relative intensities as ratios of the intensity that would be obtained from the particular standard (Cobalt K).

In some cases, pure elements are not available but compounds of known composition can be used. In this case, the intensity obtained for a particular elemental line is corrected to obtain the equivalent intensity that would be obtained from a pure element standard.

As an alternative to performing a physical experiment it is also possible to calculate all the intensities that would be measured when a beam of known energy is incident at known geometry on pure elements using a detector of known characteristics (see "Improved X-ray Spectrum Simulation for Electron Microprobe Analysis", Peter Duncumb, Ian R. Barkshire, Peter J. Statham, Microsc. Microanal. 7, 341 355, 2001). Intensities measured atone beam energy, geometry condition and detector can also be corrected to correspond to a different energy, geometry or detector. Intensity values can be obtained by processing a digitized x-ray energy spectrum. Alternatively, intensities can be measured for individual x-ray lines using a wavelength-dispersive spectrometer (WDS).

Thus, there are a variety of methods by which a database of relative pure element intensities can be obtained that conform to a particular analytical configuration. Regardless of how they are obtained, these intensities can be represented as $P_i$.

The sample of interest is then loaded into the SEM 2 and analysed according to known methods. Specifically, one or more beam energies are used to measure x-ray intensities. At step 120 the measured intensities $I^m_i$ for each beam energy, are converted to measured k-ratios, $k^m_i = I^m_i/P_i$ where the k-ratio is the ratio of the line intensity to that which would be obtained when exciting a pure element under the same conditions. Because the database of $P_i$ are relative intensity values, this first set of k-ratios will be incorrect by a constant but unknown scale factor, $B_v$, at each condition V used for measurements. Such an unsealed set of k-ratios cannot be used by structure determination software models (such as Stratagem). In order to obtain a solution for unknown parameters of the sample such models require realistic k-ratios at each condition and these are obtained by using an initial estimate for $B_v$. For example, this estimate can be obtained by using a crude estimate of the sample description (thickness and compositions of layers) and using a theoretical model (also available as part of the Stratagem software) to predict a set of theoretical k-ratios, $k^S_i$. A suitable first estimate for the beam scaling factor is then calculated at step 130 according to the following equation.

$$B_v = \mathrm{sum}_v(k^S_i)/\mathrm{sum}_v(k^m_i)$$

where the sums are over the k-ratios pertaining to a given condition V used for analysis. Other schemes could be used for obtaining a first guess, for example:

$$B_v = 1/\mathrm{sum}_v(k^m_i)$$

which observes that the sum of k-ratios is typically of the order 1.

In some circumstances, an approximate value for beam current may be available by direct or indirect measurement and this can be used as a starting guess that is refined by the iterative process.

For each condition V, effective k-ratios are calculated at step 140:

$$k_i = B_v \ast k^m_i$$

Note that k-ratios are essentially independent of beam current. In forming the k-ratio for measured intensities, we do not know the beam current for the measurement and we do not know the beam current used for the pure element standard intensities. Indeed, the pure element standard intensities may simply be ratios to that for a single element. The beam current factor includes the beam current used for the specimen and an arbitrary factor used to construct the database. The k-ratios can be thought of as having the right proportion to each other such that all that is needed to be found is the factor that converts them all into realistic k-ratios.

At step 150 these are used as input to a structure solver software model (Stratagem) which then applies an iterative solution process to find the best fit values for the unknown physical and compositional parameters of the structure, $T_j$. It will be recalled here that the fitted solution at this point is the fit for the k-ratios obtained with the estimated beam current (the beam scaling factor). The "true" solution is found when the beam scaling factor is adjusted such that the effective k-ratios represent the real k-ratios which would have been produced with reference to standards used within the same apparatus under the same conditions (including beam current). Thus, the fitted solution is a first solution and the method proceeds to attempt to find a better fit by improving the accuracy of the beam scaling factor.

At step 160, the values $T_j$ are used with the rest of the sample description to predict theoretical k-ratios, $k^S_i$ for the calculated structure.

At step 170 a comparison is made between the measured (effective) k-ratios from step 140 and those predicted at step 160. The quality of the fit between measured and predicted k-ratios is assessed. This assessment is typically the sum of the squared differences:

$$SD2 = \mathrm{sum}((k^S_i - k_i)^2)$$

although other common metrics could be used such as sum of squared relative differences or sum of squared differences weighted inversely by the expected variance of each measured k-ratio.

Having obtained a first candidate solution for both the $B_v$ and the unknowns, $T_j$, at step 180 a decision is made regarding whether a further iteration is needed depending upon the result of the comparison. Assuming this is the first time that this decision has been made it is likely that a better solution may be obtained. Thus, the process returns to step 130 and a revised value of $B_v$ is used in order to minimize SD2. Various different techniques may be used to modify $B_v$ in an attempt to efficiently arrive at a good solution. This minimization process can be achieved by a number of iterative optimization methods (see for example, Chapter 15 in "Numerical Recipes in C", Second Edition, W.H. Press et al, Cambridge University Press 1999).

When the result of the comparison at step 170 indicates that no better match can be achieved between the predicted and effective k-ratios then no further iterations are performed at step 180 and the method ends at step 190 with a final solution including values for each unknown. One such unknown is the calculated beam current factor for this solution.

In iterative schemes that attempt to improve the solution at each iteration, the success of the iterative scheme can be observed by monitoring SD2 values at each iteration to make sure the results are not diverging. Rather than evaluate SD2 for all k-ratios, separate values of SD2 can be evaluated for each excitation condition V and used to drive the choice of the next $B_v$. For example, in some problems, a simple substitution scheme will work where the next trial value of $B_v$ is calculated using the latest predicted k-ratios corresponding to condition V:

$$B_v = \text{sum}_v(k^s_i)/\text{sum}_v(k^m_i)$$

If use of this scale factor in the next iteration produces an increase in SD2 for k-ratios corresponding to condition v, then the previous value of $B_v$ is retained for the subsequent iteration. It will be appreciated that other schemes may be used, as may a "brute force" method in which a series of candidate values for beam current factor are investigated and the value that gives the best fit is ultimately chosen.

A practical example is now discussed. The sample to be analysed in this example consists of a homogeneous layer of silicon oxide of unknown composition likely to be between 10 and 100 nm thick on a substrate of silicon. Both the composition and the thickness of the layer are to be determined with no direct or indirect measurement of beam current. Since the mass fractions of Si and O in the layer will add to unity, there is effectively one unknown for composition, one unknown for thickness and one unknown for beam current. There are 2 x-ray lines that can be measured: O K and Si K. If a single excitation condition is used (that is, at a particular beam energy and beam-sample-detector geometry), there would therefore be 2 measurements and 3 unknowns so solution of the structure would be impossible.

However, if data are acquired at 2 keV and 5 keV, there would be 4 measurements available and 4 unknowns (2 beam current factors, 1 thickness and 1 concentration) so the problem is soluble if the measurements all provide some independent information.

The first stage in the method of FIG. 4 is the use of a database to obtain some relevant x-ray intensity data for the two elements of interest under the same conditions. Table 1 shows the intensities corresponding to the pure elements oxygen and silicon at 2 keV and 5 keV beam energy on a particular detector. The intensities are the counts that would be recorded for a fixed acquisition time for the same incident beam current in each case and for the same beam-sample-detector geometry. This is effectively the database entries showing the relative intensities for the elements involved.

TABLE 1

| keV | O K | Si K |
|---|---|---|
| 2 | 6161528 | 92224 |
| 5 | 28614503 | 19783904 |

In this case, the database has been generated by theoretical calculation rather than direct measurement. The same geometry and detector configuration are used that are used to make measurements upon the sample.

The sample of unknown structure is first exposed to a 2 keV beam at one particular beam current and a spectrum is acquired (step 110). This spectrum is analysed to obtain counts for O K and Si K peaks. The sample is then exposed to a 5 keV beam at a different beam current, a spectrum is acquired and counts are obtained for O K and Si K peaks. The data are shown in Table 2.

TABLE 2

| keV | O K | Si K |
|---|---|---|
| 2 | 416643 | 12456 |
| 5 | 54940 | 941318 |

The data are then converted to unsealed measured k-ratios using the relationship discussed earlier (step 120), $k^m_i = I^m_i/P_i$, as shown in Table 3.

TABLE 3

| keV | O K | Si K |
|---|---|---|
| 2 | 0.06762 | 0.13506 |
| 5 | 0.00192 | 0.04758 |

It is assumed that the measurements at each beam energy are subject to different and unknown beam current factors which need to be estimated.

As a starting guess for the structure it is assumed that there exist equal mass fractions of Si and O in the layer, together with a 10 nm layer thickness. These estimates are then used as inputs into the Stratagem software to predict expected values for k-ratios from such a structure at 2 keV and 5 keV. The predicted k-ratios are given in Table 4.

TABLE 4

| keV | O K | Si K |
|---|---|---|
| 2 | 0.1037 | 0.5888 |
| 5 | 0.0169 | 0.974 |

At step 130 these rough estimates of typical k-ratios are used to calculate beam current factors using the relationship $B_v = \text{sum}_v(k^s_i)/\text{sum}_v(k^m_i)$. The calculated data are shown in Table 5.

TABLE 5

| keV | $B_V$ |
|---|---|
| 2 | 3.417 |
| 5 | 20.02 |

These beam current factors are then applied to the measured k-ratios at step 140 to obtain the effective k-ratios using the relationship $k_i = B_v * k^m_i$. These effective k-ratios are shown in Table 6.

TABLE 6

| keV | O K | Si K |
|---|---|---|
| 2 | 0.2310 | 0.4615 |
| 5 | 0.0384 | 0.9525 |

The calculated values from Table 6 are then entered into the Stratagem structure solver model, together with other data describing known parameters of the sample and the beam-sample-detector geometry. An iteration procedure (step 150) within the model produces a result for thickness and concentrations for the unknown layer as set out in Table 7.

TABLE 7

| | Result |
|---|---|
| Thickness nm | 21.34 |
| O | 0.5077 |
| Si | 0.4923 |

This is the first solution according to the model using the first beam scaling factor. These data are then input into the predictor part of the Stratagem software at step 160 to produce a predicted set of k-ratios for this structure. The predicted k-ratios are shown in Table 8.

TABLE 8

| keV | O K | Si K | SD2 |
|---|---|---|---|
| 2 | 0.2305 | 0.4667 | 0.00002773 |
| 5 | 0.0394 | 0.9415 | 0.00012116 |

The right hand column shows sum of squared differences (SD2) with the effective k-ratios of Table 6 at each beam voltage. The SD2 values are used in a comparison step 170. A decision is then made at step 180 regarding whether an improved result should be sought by a further iteration so as to seek a further minimization of SD2.

If a further iteration is required then the method returns to step 130 in FIG. 4 where new beam current factors are calculated from the predicted k-ratios of Table 8 as above, using the relationship $sum_v(k^s_i)/sum_v(k^m_i)$. The revised beam scaling factors are shown in Table 9.

TABLE 9

| keV | $B_V$ |
|---|---|
| 2 keV | 3.440 |
| 5 keV | 19.82 |

These factors are then used to form a new set of effective k-ratios (step 140) as shown in Table 10.

TABLE 10

| keV | O K | Si K |
|---|---|---|
| 2 | 0.2326 | 0.4646 |
| 5 | 0.0380 | 0.9429 |

When these input k-ratios are used as input to the Stratagem solver (step 150), the following results obtained are shown in Table 11.

TABLE 11

| | Result |
|---|---|
| Thickness nm | 21.56 |
| O | 0.5083 |
| Si | 0.4917 |

This is the second solution according to the model using the second beam scaling factor. These data are then input into the predictor part of the Stratagem software at step 160 to produce a predicted set of k-ratios for this structure and therefore test this solution. The predicted k-ratios are shown in Table 12.

TABLE 12

| keV | O K | Si K | SD2 |
|---|---|---|---|
| 2 | 0.2331 | 0.4654 | 0.00000089 |
| 5 | 0.0399 | 0.9408 | 0.00000765 |

The SD2 values are much smaller and show that this solution is much better than when using the first pair of beam current factors. Further iterations can be used where $B_v$ values are adjusted to minimise the sum of squared differences even further.

Thus, even though the beam current factors are not known at the start, the iterative process has found beam factors of 3.44 and 19.82 and when these factors are used to correct the measured k-ratios, the Stratagem solver gives thickness 21.56 nm and mass fractions of 0.5083 and 0.4917 for O and Si respectively.

The invention claimed is:
1. A method, implemented in a processor, of calculating the structure of an inhomogeneous sample in which an electron beam is used to cause excitation of x-rays from the sample under known conditions of beam energy and geometry with respect to the sample, and wherein the beam current is unknown, the method comprising:
  i) obtaining measured x-ray intensity data for the sample, the data corresponding to one or more sets of beam conditions and beam currents, and inputting the measured x-ray intensity data into the processor;
  ii) obtaining comparative x-ray intensity data for samples having known structures and inputting the comparative x-ray intensity data into the processor;
  iii) estimating, in the processor, a beam current factor for each beam condition;
  iv) calculating, in the processor, effective x-ray intensity data for each of the sets of conditions using the measured and comparative x-ray intensity data and the beam current factor;
  v) calculating, in the processor, the structure of the sample for each of the sets of conditions using the effective x-ray intensity data;
  vi) predicting, in the processor, x-ray intensity data corresponding to the calculated structure;
  vii) comparing, in the processor, the predicted and effective x-ray intensity data; and
  viii) repeating steps (iii) to (vii) in the processor using beam current factors revised in accordance with step (vii) until the predicted and effective x-ray intensity data achieve a predetermined similarity criterion.

2. A method according to claim 1, wherein the structure comprises one or each of the physical dimensions and composition of the sample.

3. A method according to claim 1, wherein the sample is a multi-layered sample.

4. A method according to claim 1, wherein the calculation of the structure according to step (v) uses structure data defining physical parameters and composition parameters of the structure.

5. A method according to claim 4, wherein part of the structure data comprises unknown physical parameters or unknown composition parameters or unknown physical and composition parameters.

6. A method according to claim 1, wherein the comparative x-ray intensity data comprises data normalised with respect to a particular element.

7. A method according to claim 1, wherein the comparative x-ray intensity data are obtained by a method selected from the group of: calculation according to a model, physical measurement of standard samples of pure elemental composition, physical measurement of standard samples of compounds of known composition wherein corresponding pure elemental contributions are calculated.

8. A method according to claim 1, wherein the processor calculates an initial estimate of the beam current in step (iii) by:
   a) using structure data defining an assumed structure of the sample to calculate assumed x-ray intensity data for the sample, the structure data including assumed values for any unknown parameters of physical structure or composition; and,
   b) dividing the sum of the values for the assumed x-ray intensity data by the sum of the values of the measured x-ray intensity data for the particular set of conditions and beam current in question.

9. A method according to claim 1, wherein the x-ray intensity data are expressed as k-ratios and wherein an initial estimate of the beam current in step (iii) is calculated as the inverse of the sum of the measured x-ray intensity data.

10. A method according to claim 1, wherein the predicted x-ray intensity data are expressed as k-ratios.

11. A method according to claim 1, wherein the processor performs the calculation of the structure in step (v) by a structure solver model.

12. A method according to claim 1, wherein the comparison step (vii) includes calculating, in the processor, the sum of the squared differences between the values of the predicted and effective x-ray intensity data.

13. A method according to claim 1, wherein the similarity criterion is met when the difference between the values of the predicted and effective x-ray intensity data does not reduce upon further repetitions according to step (viii).

14. A method according to claim 1, further comprising investigating, in the processor, the calculated structure by representing the predicted k-ratios as a vector of M dimension and the unknown parameters of the structure, including the beam current factor, as a vector of N dimension and using numerical differentiation of a theoretical model for x-ray emission so as to form a Jacobian matrix of partial derivatives relating the k-ratios and the unknown structure parameters; and calculating a condition number relating to the degree of solubility of the matrix.

15. A method according to claim 14, further comprising comparing, in the processor, the condition number with a predetermined threshold so as to indicate to a user whether the method is soluble for a given set of experimental conditions.

16. A computer program comprising;
a non-transitory computer readable storage medium; and
program code, stored on the medium, adapted to perform the steps of the method of claim 1 when the program is executed upon a computer.

17. A system for calculating the structure of an inhomogeneous sample in which an electron beam is used to cause excitation of x-rays from the sample under known conditions of beam energy and geometry with respect to the sample, and wherein the beam current is unknown, the system comprising:
   a source of data taken from the sample; and
   a processor in communication with the source, the processor being configured for:
   i) obtaining measured x-ray intensity data for the sample, the data corresponding to one or more sets of beam conditions and beam currents;
   ii) obtaining comparative x-ray intensity data for samples having known structures;
   iii) estimating a beam current factor for each beam condition;
   iv) calculating effective x-ray intensity data for each of the sets of conditions using the measured and comparative x-ray intensity data and the beam current factor;
   v) calculating the structure of the sample for each of the sets of conditions using the effective x-ray intensity data;
   vi) predicting x-ray intensity data corresponding to the calculated structure;
   vii) comparing the predicted and effective x-ray intensity data; and
   viii) repeating steps (iii) to (vii) using beam current factors revised in accordance with step vii) until the predicted and effective x-ray intensity data achieve a predetermined similarity criterion.

18. A system according to claim 17, wherein the processor is configured such that the structure comprises one or each of the physical dimensions and composition of the sample.

19. A system according to claim 17, wherein the processor is configured to accommodate a multi-layered sample.

20. A system according to claim 17, wherein the processor is configured such that the calculation of the structure according to step (v) uses structure data defining physical parameters and composition parameters of the structure.

21. A system according to claim 20, wherein the processor is configured such that part of the structure data comprises unknown physical parameters or unknown composition parameters or unknown physical and composition parameters.

22. A system according to claim 17, wherein the processor is configured such that the comparative x-ray intensity data comprises data normalised with respect to a particular element.

23. A system according to claim 17, wherein the processor is configured such that the comparative x-ray intensity data are obtained by a method selected from the group of: calculation according to a model, physical measurement of standard samples of pure elemental composition, physical measurement of standard samples of compounds of known composition wherein corresponding pure elemental contributions are calculated.

24. A system according to claim 17, wherein the processor is configured to calculate an initial estimate of the beam current in step (iii) by:
   c) using structure data defining an assumed structure of the sample to calculate assumed x-ray intensity data for the sample, the structure data including assumed values for any unknown parameters of physical structure or composition; and d) dividing the sum of the values for the assumed x-ray intensity data by the sum of the values of the measured x-ray intensity data for the particular set of conditions and beam current in question.

25. A system according to claim 17, wherein the processor is configured such that the x-ray intensity data are expressed as k-ratios and wherein an initial estimate of the beam current in step (iii) is calculated as the inverse of the sum of the measured x-ray intensity data.

26. A system according to claim 17, wherein the processor is configured such that the predicted x-ray intensity data are expressed as k-ratios.

27. A system according to claim 17, wherein the processor is configured to perform the calculation of the structure in step (v) by a structure solver model.

28. A system according to claim 17, wherein the processor is configured such that the comparison step (vii) includes calculating the sum of the squared differences between the values of the predicted and effective x-ray intensity data.

29. A system according to claim 17, wherein the processor is configured such that the similarity criterion is met when the difference between the values of the predicted and effective x-ray intensity data does not reduce upon further repetitions according to step (viii).

30. A system according to claim 17, wherein the processor is configured for investigating the calculated structure by representing the predicted k-ratios as a vector of M dimension and the unknown parameters of the structure, including the beam current factor, as a vector of N dimension and using numerical differentiation of a theoretical model for x-ray emission so as to form a Jacobian matrix of partial derivatives relating the k-ratios and the unknown structure parameters; and calculating a condition number relating to the degree of solubility of the matrix.

31. A system according to claim 30, wherein the processor is configured for comparing the condition number with a predetermined threshold so as to indicate to a user whether the method is soluble for a given set of experimental conditions.

* * * * *